United States Patent [19]

VandenBerg

[11] Patent Number: Plant 6,988

[45] Date of Patent: Aug. 15, 1989

[54] CHRYSANTHEMUM PLANT NAMED TOLIMA

[75] Inventor: Cornelis P. VandenBerg, Salinas, Calif.

[73] Assignee: Yoder Brothers, Inc., Barberton, Ohio

[21] Appl. No.: 247,524

[22] Filed: Sep. 22, 1988

[51] Int. Cl.[4] ..... A01H 5/00

[52] U.S. Cl. ..... Plt./77

[58] Field of Search ..... Plt./77

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A chrysanthemum plant named Tolima particularly characterized by its flat capitulum form; decorative capitulum type; white ray floret color; diameter across face of capitulum of up to 8 cm at maturity; good flower form and excellent flower form retention, short plant height with spreading and prolific branching pattern; average natural season flower date of August 28 in Salinas, Calif. and September 28 in Hightstown, N.J.; uniform seven week photoperiodic flowering response to short days in photoperiodic controlled flowering programs; and durable, uniform performance in outside fall flowerings and in spring small pot flowering programs.

3 Drawing Sheets

The present invention comprises a new and distinct cultivar of chrysanthemum, botanically known as *Dendranthema grandiflora,* and referred to by the cultivar name Tolima.

Tolima, identified as 85-010002, was originated from a cross made by the inventor, Cornelis P. VandenBerg, in a controlled breeding program in Salinas, Calif., in 1985.

The female parent and the male parent of Tolima were both unnamed seedlings, identified respectively as 83-M05022 and 82-M49004. Tolima was discovered and selected as one flowering plant within the progeny of the stated cross by Cornelis P. VandenBerg in January 1986, in a controlled environment in Salinas, Calif.

The first act of asexual reproduction of Tolima was accomplished when vegetative cuttings were taken from the initial selection in April 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Tolima are firmly fixed and are retained through successive generations of asexual reproduction.

Tolima has not been observed under all possible environmental conditions. The phenotype may vary significantly with variations in environment such as temperature, light intensity and daylength.

The following observations, measurements and comparisons describe plants grown in a controlled open area in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Tolima, which, in combination, distinguish this chrysanthemum as a new and distinct cultivar:

1. Flat capitulum form.
2. Decorative capitulum type.
3. White ray floret color.

4. Diameter across face of capitulum up to 8 cm at maturity.
5. Good flower form and excellent flower form retention.
6. Short plant height.
7. Spreading and prolific branching pattern.
8. Average natural season flower date of August 28 in Salinas, Calif., and September 28 in Hightstown, N.J.
9. Uniform seven week photoperiodic flowering response to short days in photoperiodic controlled flowering programs.
10. Durable, uniform performance in outside fall flowerings and in spring small pot flowering programs.

The accompanying photographic drawings show typical inflorescence and leaf characteristics of Tolima, with the colors being as nearly true as possible with illustrations of this type. Sheet 1 is a color photograph of Tolima grown as a pinched spray pot mum. Sheet 2 is a black and white photograph of three views of the inflorescence of Tolima. Sheet 3 is a black and white photograph showing the upper and under sides of the leaves of Tolima at three stages of development (mature, intermediate and immature).

Of the commercial cultivars known to the inventor, the most similar in comparison to Tolima is Encore, disclosed in the inventor's pending plant patent application, Ser. No. 938,889. Reference is made to attached Chart A, which compares certain characteristics of Tolima to the same characteristics of Encore.

Similar traits are ray floret color, capitulum form and type, branching pattern, plant height and controlled flowering response. Tolima has a significantly larger diameter of capitulum with a better flower form and much better flower form retention than Encore. Tolima has a slightly slower natural season flowering response on the east coast than Encore.

In the following description color references are made to The Royal Horticultural Society Colour Chart. The clear white ray floret color of Tolima is not represented in the RHS Colour Chart. The color values were determined on plant material grown in a controlled greenhouse environment in Salinas, Calif. on May 20, 1988.

Classification:

*Botanical.—Dendranthema grandiflora,* cv Tolima

*Commercial.*—Decorative spray pot mum and garden mum.

INFLORESCENCE

A. Capitulum:

*Form:* Flat.

*Type:* Decorative.

*Diameter across face:* Up to 8 cm at maturity.

B. Corolla of ray florets:

*Color (general tonality from a distance of three meters):* White.

*Color (upper surface):* White, with center of flower closest to 150D.

*Color (under surface):* White.

*Shape:* Flat, straight, narrow, oblong.

C. Corolla of disc florets:

*Color (mature):* Closest to 2A.

*Color (immature):* Closest to 150C. Very few disc florets, covered by ray florets.

D. Reproductive organs:

*Androecium:* Present on disc florets only; very scant pollen.

*Gynoecium:* Present on both ray and disc florets.

PLANT

A. General appearance:

*Height:* Short.

*Branching pattern;* Spreading and prolific.

B. Foliage:

*Color (upper surface):* 137A.

*Color (under surface):* 137B.

*Shape:* Small, lobed.

CHART A

COMPARISONS MADE OF PLANTS GROWN UNDER NATURAL SEASON OUTDOOR CONDITIONS IN SALINAS, CALIFORNIA AND IN HIGHTSTOWN, NEW JERSEY

COMPARISON OF TOLIMA AND ENCORE

| Cultivar | Tolima | Encore |
|---|---|---|
| Ray Floret Color | White | White |
| Capitulum Form and Type | Flat Decorative | Flat Decorative |
| Branching Pattern | Spreading and Prolific | Spreading and Prolific |
| Diameter Across Face of Capitulum | Up to 8 cm | 6 cm |
| Plant Height | Short | Short |
| Controlled Response | 7 Weeks | 7 Weeks |
| Average Natural Season Flowerdate: | | |
| In Salinas, CA | August 28 | August 30 |
| In Hightstown, NJ | September 28 | September 24 |

I claim:

1. A new and distinct chrysanthemum plant named Tolima, as described and illustrated.

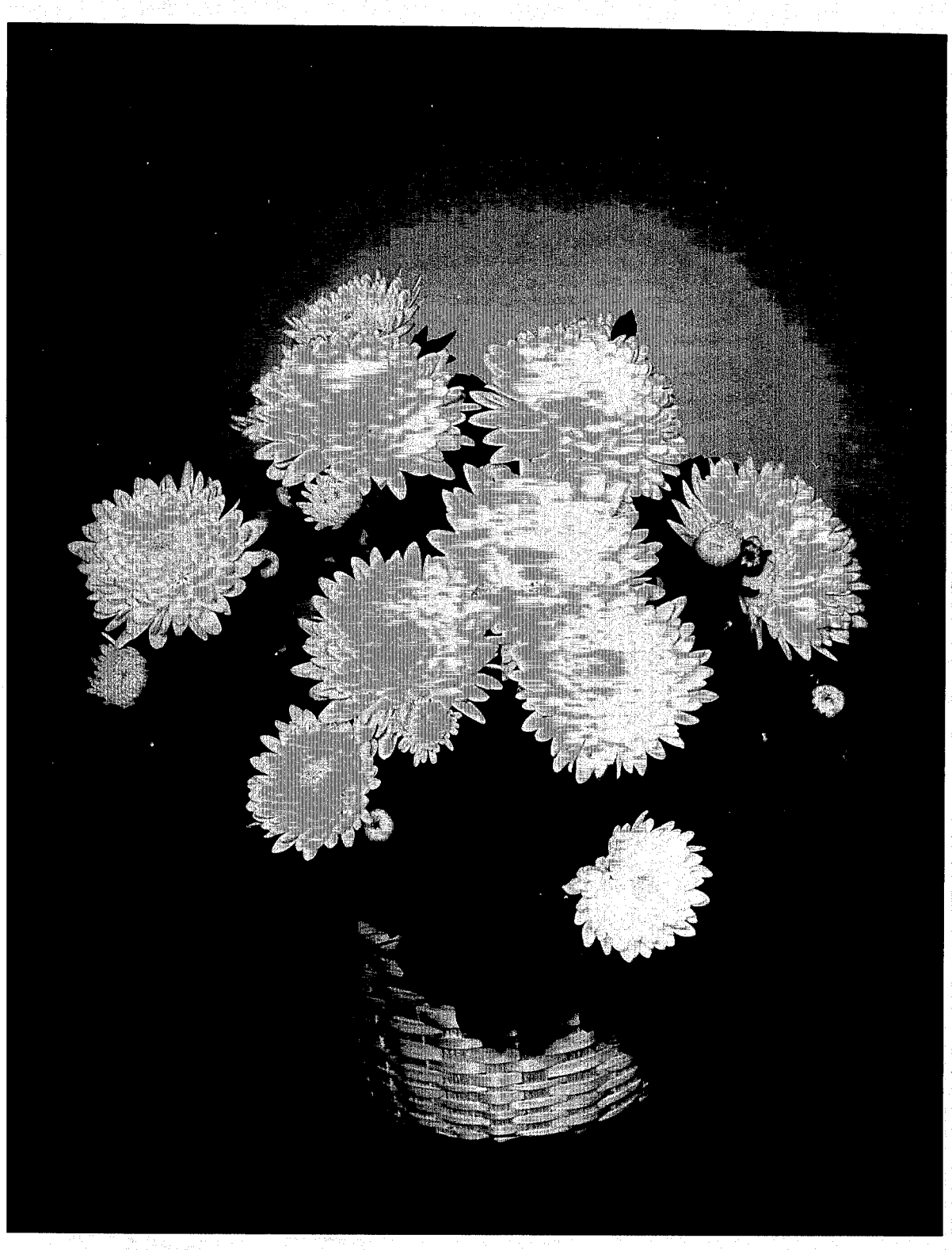

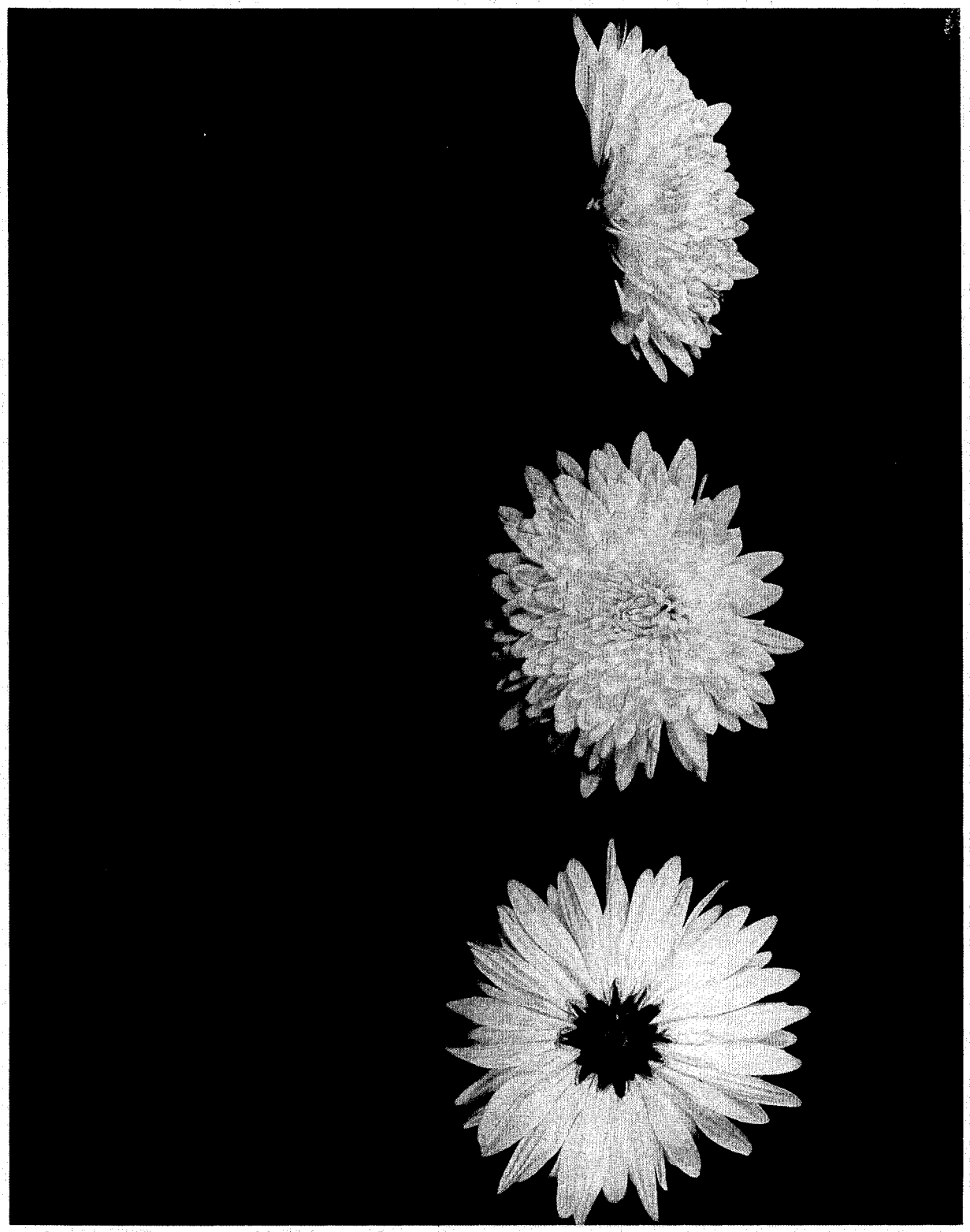

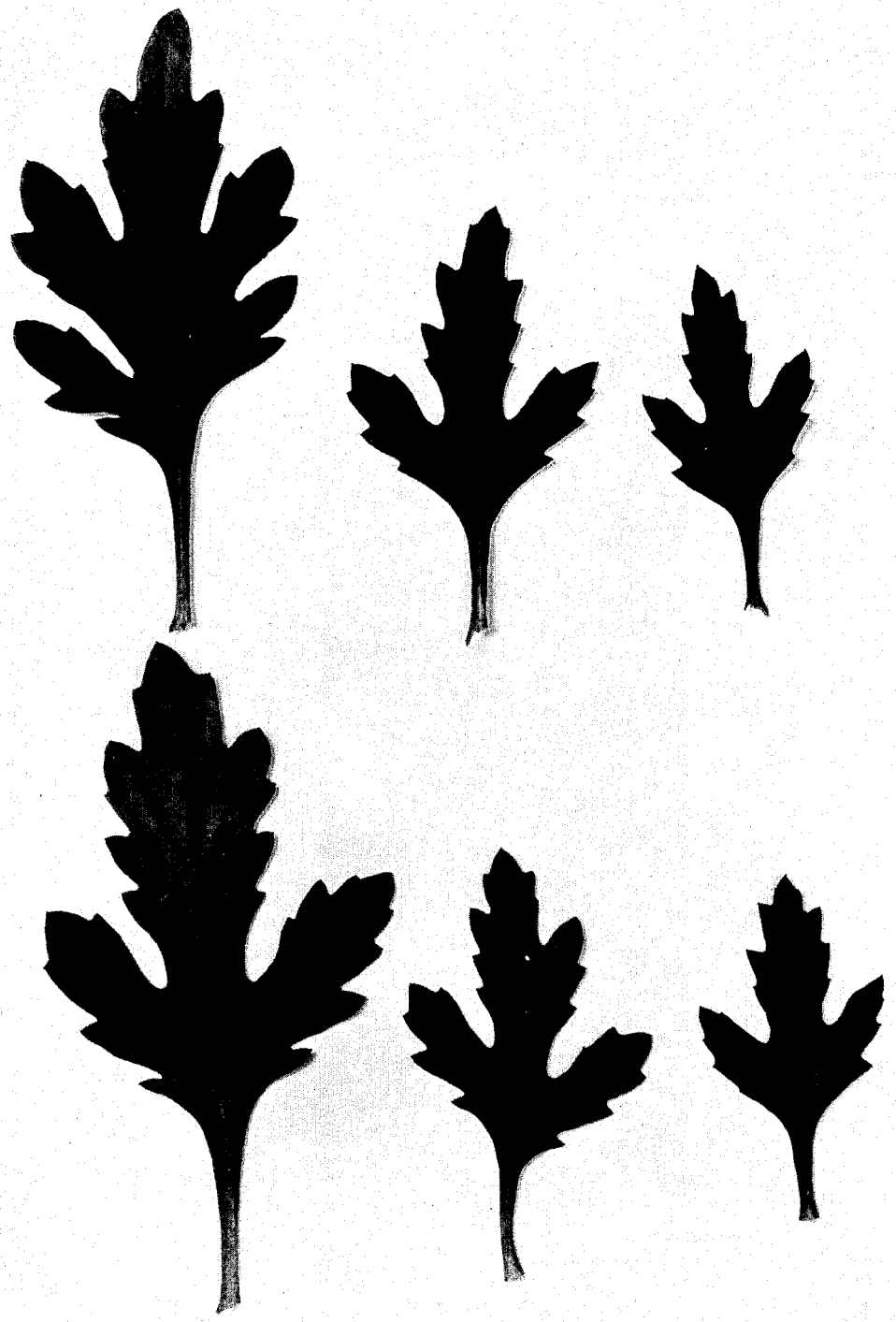

* * * * *